(12) United States Patent
Hoppe et al.

(10) Patent No.: US 10,698,055 B2
(45) Date of Patent: Jun. 30, 2020

(54) METHOD, NEURAL NETWORK, AND MAGNETIC RESONANCE APPARATUS FOR ASSIGNING MAGNETIC RESONANCE FINGERPRINTS

(71) Applicant: Siemens Healthcare GmbH, Erlangen (DE)

(72) Inventors: Elisabeth Hoppe, Erlangen (DE); Andreas Maier, Erlangen (DE); Josef Pfeuffer, Kunreuth (DE)

(73) Assignee: Siemens Healthcare GmbH, Erlangen (DE)

(*) Notice: Subject to any disclaimer, the term of this patent is extended or adjusted under 35 U.S.C. 154(b) by 33 days.

(21) Appl. No.: 15/945,964

(22) Filed: Apr. 5, 2018

(65) Prior Publication Data

US 2018/0292484 A1 Oct. 11, 2018

(30) Foreign Application Priority Data

Apr. 5, 2017 (EP) .................................. 1 71 64986

(51) Int. Cl.
| | | |
|---|---|---|
| *G01V 3/00* | (2006.01) | |
| *G01R 33/48* | (2006.01) | |
| *G01R 33/50* | (2006.01) | |
| *G16H 50/20* | (2018.01) | |
| *G06K 9/00* | (2006.01) | |
| *G01R 33/56* | (2006.01) | |
| *G16H 30/40* | (2018.01) | |

(Continued)

(52) U.S. Cl.
CPC ......... *G01R 33/4828* (2013.01); *G01R 33/50* (2013.01); *G01R 33/5602* (2013.01); *G01R 33/5608* (2013.01); *G01R 33/5614* (2013.01); *G06K 9/00496* (2013.01); *G06K 9/66* (2013.01); *G06N 3/04* (2013.01); *G06N 3/0454* (2013.01); *G06N 3/08* (2013.01); *G06N 3/084* (2013.01); *G16H 30/40* (2018.01); *G16H 50/20* (2018.01); *G01R 33/5613* (2013.01)

(58) Field of Classification Search
CPC .............. G01R 33/543; G01R 33/5659; G01R 33/3415; G01R 33/36; A61B 5/055
USPC ....................................................... 324/309
See application file for complete search history.

(56) References Cited

U.S. PATENT DOCUMENTS

| | | | |
|---|---|---|---|
| 6,975,894 B2 * | 12/2005 | Wehrli ................... | A61B 5/417 600/407 |
| 2010/0166273 A1 * | 7/2010 | Wismuller ............ | G06T 7/0012 382/131 |

(Continued)

OTHER PUBLICATIONS

FISP.pdf Magnetic Resonance—Technology Information Portal Member of SoftWays' Medical Imaging Group—MR-TIP • Radiology-TIP • US-TIP • Copyright © 2003-2018 SoftWays. All rights reserved. [ Aug. 5, 2019] Terms of Use | Privacy Policy | Advertising; Publication year: 2003.*
Voxel.pdg downloaded from NET on Jan. 5, 2020 published Dec. 9, 2019.*
Jiang, et al; "MR Fingerprinting Using Fast Imaging with Steady State Precession (FISP) with Spiral Readout"; Magnetic Resonance in Medicine; vol. 74; pp. 1621-1631, (2015).

(Continued)

*Primary Examiner* — Walter L Lindsay, Jr.
*Assistant Examiner* — Frededrick Wenderoth
(74) *Attorney, Agent, or Firm* — Schiff Hardin LLP

(57) ABSTRACT

In a method for determining magnetic resonance (MR) parameters, an MR fingerprint of a voxel is acquired by execution of a pulse sequence, the MR fingerprint is provided as an input into the input layer of a trained neural network, and at least one MR parameter relating to the MR fingerprint is provided at the output layer of the neural network.

15 Claims, 6 Drawing Sheets

(51) Int. Cl.
  *G06N 3/08* (2006.01)
  *G06N 3/04* (2006.01)
  *G01R 33/561* (2006.01)
  *G06K 9/66* (2006.01)

(56) References Cited

U.S. PATENT DOCUMENTS

| | | | |
|---|---|---|---|
| 2014/0142892 A1* | 5/2014 | Song | G06F 17/18 702/176 |
| 2015/0297101 A1* | 10/2015 | Hernandez-Garcia | G01R 33/56563 600/419 |
| 2015/0302297 A1 | 10/2015 | Griswold et al. | |
| 2015/0346301 A1* | 12/2015 | Cauley | G01R 33/4828 324/309 |
| 2016/0061922 A1 | 3/2016 | Grodzki et al. | |
| 2016/0140326 A1* | 5/2016 | Karthikeyan | G16C 20/20 703/1 |

OTHER PUBLICATIONS

Zhang, et al; "Towards End-to-End Speech Recognition with Deep Convolutional Neural Networks"; depenarXiv: 1701.02720v1 [cs.CL] Jan. 10, 2017.
Jain et al.: Statistical Pattern Recognition: A Review; IEEETRANSACTIONS on Pattern Analysis and Machine Intelligence, IEEE Computer Society; USA; vol. 22; No. 1; pp. 4-37; (2000).
Ma, et al.: "Magnetic resonance fingerprinting"; Nature; vol. 495, Nr. 7440; pp. 187-192; (2013).
Cauley et al.,: "Fast Group Matching for MR Fingerprinting Reconstruction"; Magn. Reson.Med. 74; pp. 523-528; (2015).
Wang, et al: "MRF Denoising With Compressed Sensing and Adaptive Filtering"; arXiv:1401.0670v1 [cs.IT] Jan. 3, 2014.
Golkov et al.: "q-Space Deep Learning: Twelve-Fold Shorter and Model-Free Diffusion MRI Scans"; IEEE Transactions on Meidcal Imaging, vol. 35; No. 5; pp. 1344-1351; (2016).

* cited by examiner

METHOD, NEURAL NETWORK, AND MAGNETIC RESONANCE APPARATUS FOR ASSIGNING MAGNETIC RESONANCE FINGERPRINTS

BACKGROUND OF THE INVENTION

Field of the Invention

The present invention concerns a method and computer for determining MR (magnetic resonance) parameters on the basis of MR fingerprints.

Description of the Prior Art

MR parameters are important for magnetic resonance techniques, for example for magnetic resonance tomography, an imaging method for displaying body tissue. Some nuclei of the tissue to be examined have intrinsic angular momentum (nuclear spin) and are consequently magnetic dipoles. Following the application of a static magnetic field, these nuclei are aligned by a longitudinal magnetization in the direction of the static field. As a result of a briefly applied radio frequency (RF) alternating field, the longitudinal magnetization can be deflected from the direction of the static field, in other words converted partially or wholly into a transverse magnetization. Once the radio frequency alternating field has been switched off, the transverse magnetization decreases, in other words the nuclear spins are again oriented parallel to the static magnetic field. This so-called relaxation occurs with a characteristic decay time. During this relaxation, the nuclei emit RF signals, called MR signals, that are detected by reception coils. Different types of tissue are distinguished by their MR parameters or their MR parameter combinations, for example in the longitudinal relaxation time T1 and/or in the transversal relaxation time T2.

With MR Fingerprinting (MRF), characteristic time series are obtained as the MR signal per grid point (voxel) in a three-dimensional grid. These time series are called the MR fingerprint of the voxel. Using a comparison with simulated time series, in which the MR parameters are known for the simulation, the MR parameters of the voxel may be determined.

The method for obtaining these time series is described for example in Jiang Y, Ma D, Seiberlich N, Gulani V, Griswold M A, "MR Fingerprinting Using Fast Imaging with Steady State Precession (FISP) with Spiral Readout", Magnetic Resonance in Medicine 74:1621-1631 (2015). In the method described there, the MR signals are measured using an MRF-FISP pulse sequence, in which a series of FISP scans follows an adiabatic inversion pulse. In the MRF-FISP pulse sequence a sinusoidal distribution of setting angles and repetition times is used in a Perlin noise pattern. Interleaving of a spiral trajectory of a variable density is used in each repetition. The spiral trajectory is zero moment-compensated. Twenty four interleaves are required in order to sample the center of the k-space and 48 interleaves for an area of 256×256. Other recording methods, for example Cartesian or radial methods, are also possible for measuring the MR signals. The temporal sequence of gradients to be switched, RF pulses to be irradiated and signal recording windows of a recording method is specified by the associated pulse sequence respectively.

To obtain the properties of the tissue, such as, for example, the T1 and T2 relaxation times, the measured time series, in other words the MR fingerprint of the tissue, is matched with a previously simulated MR fingerprint from a dictionary by means of pattern recognition in the imaging MRF method. The dictionary with the MR fingerprints is constructed in advance and comprises the simulated fingerprints for possible combinations of all MR parameters. The dictionary is generated using Bloch equations and the same acquisition parameters as for the measurement, such as, for example a distribution of flip angles, a phase of the RF pulses or repetition times.

By matching, those simulated time series are chosen from the dictionary which best match the measured time series. Since for the simulated time series, the T1 and T2 relaxation times are known from the dictionary, these parameters can also be assigned to the tissue from the corresponding voxel.

The known methods for pattern recognition for matching the measured fingerprints with the previously stored fingerprints can be described as follows:

1) Ma D, Gulani V, Seiberlich N, Liu K, Sunshine J L, Duerk J L, Griswold M A, "Magnetic Resonance Fingerprinting", Nature 2013; 495: 187-192, use template matching. For this purpose, a vector scalar product is calculated between the measured time series and all individual time series of the dictionary. The parameters of those time series having the greatest scalar product are selected and assigned to the corresponding voxels.

2) Cauley S F, Setsompop K, Ma D, Jiang Y, Ye H, Adalsteinsson E, Griswold M A, Wald L L, "Fast Group Matching for MR Fingerprinting Reconstruction", Magn. Reson. Med. 2015 August; 74(2):523-528 propose a Fast Group Matching method to accelerate matching. This is not achieved by comparing a measured time series with the entire dictionary. Instead, similar time series are grouped together. In this way, M time series from the dictionary are distributed among N groups. Each group has M/N elements.

Grouping is carried out by first choosing an initial signal $S_0$. The initial signal $S_0$ is compared with all other time series of the dictionary. The M/N signals most correlated with the initial signal are used to generate the first group. A new signal $S_1$ is generated, in other words a mean signal of the first group, which from now on best represents the entries in the first group. A smaller group plane of a Principal Component Analysis (PCA) is calculated using singular value analysis. These steps are repeated until all dictionary elements are distributed.

An acquired time series is matched with this compressed dictionary by matching the time series against all representative group signals $S_1, \ldots, S_N$. The groups having the greatest matches are chosen. The remaining groups are then evaluated by a PCA projection. The best result and its parameters are then chosen for the voxel.

SUMMARY OF THE INVENTION

An object of the present invention is to improve and accelerate determination of MR parameters on the basis of MR fingerprints.

According to a first aspect of the invention, the object is achieved by a method for determining MR parameters, having the steps of acquiring an MR fingerprint of a voxel by execution of a pulse sequence, providing the MR fingerprint as an input into the input layer of a trained neural network, and at least one MR parameter relating to the MR fingerprint is provided as an output at the output layer of the trained neural network.

The method achieves the technical advantage that speed of quantification is increased, and a dictionary is no longer required for the step of quantification of the MR parameters whose storage space requirement increases with the possible parameter combinations contained therein. The dictionary is implicitly represented by the trained neural network, but—compared to the dictionary—this has a constant storage size. Significantly less storage space is therefore required with the inventive method since the previously required storage space for the dictionary (for the reference signals) is omitted.

Basically, during MR imaging, different radio frequency signals are compiled over a period in order to identify a signal evolution for the volume. A spatial resolution (for assigning the acquired signals to a voxel) is achieved by means of linear location-dependent gradient fields. Since different tissue types (for example tumor tissue) can generate different RF signals, methods of pattern recognition in the signal time characteristic are frequently used in the prior art for characterization of the tissue type.

The basic idea underlying MR Fingerprinting (MRF) consists in that unique signal evolutions—what are known as fingerprints—can be generated for different tissue regions and/or tissue types using a suitable measuring and reconstruction pattern. An MR fingerprint includes the application of a series of varied pulse sequence blocks, which generate a particular signal evolution signature, in other words the MR fingerprint, which is specific to a particular combination of parameters and resonance types in a volume. Processing of the received MRF signals no longer includes a conventional reconstruction, but matching with reference signals.

In the prior art, processing following the MR scan can include a pattern recognition algorithm to match the compiled fingerprints with predicted signal evolutions from a predefined dictionary, and this requires significant computing and storage effort.

Instead of the pattern recognition algorithm, an alternative method is used in the method proposed here, in which use is made of a neural network for determining the MR parameters.

Neural networks are already used in the field of MR technology. Use of a neural network is therefore described for example in U.S. patent application Ser. No. 14/682,220 for generating pulse sequences, but not for categorizing measured MR fingerprints.

In a technically advantageous embodiment of the method, the pulse sequence is an MRF-FISP pulse sequence. This has, for example, the technical advantage that MR fingerprints can be efficiently obtained.

In a further technically advantageous embodiment of the method, the at least one MR Parameter comprises a T1 relaxation time and/or a T2 relaxation time. This has, for example, the technical advantage that the relaxation times of the voxel can be determined quickly.

In a further embodiment of the method, a number of MR fingerprints of adjacent voxels are provided as inputs into the input layer and at least one shared MR parameter is emitted as an output for the multiple MR fingerprints at the output layer. This has the technical advantage that more stable estimation or error estimation is obtained.

In a further embodiment of the method, a single MR fingerprint of a voxel is provided as an input into the input layer and a number of MR parameters are emitted as outputs for adjacent voxels at the output layer. This has the technical advantage that a resolution can be improved.

In a further embodiment of the method, a contrast between two MR fingerprints is evaluated by means of the neural network. This has the technical advantage that a recording sequence can be changed such that the contrast is maximal.

In a further embodiment of the method, the method is applied to a large number of adjacent voxels. This has the technical advantage that maps and images of the corresponding MR parameters can be determined.

According to a further aspect of the invention, a non-transitory, computer-readable storage medium is provided, which is encoded with programming instructions that, when the storage medium is loaded into a computer that includes a neural network, cause the computer to implement any or all of the embodiments of the method according to the invention, as described above.

According to a further aspect of the invention, the object is achieved by a neural network having an input layer that receives an MR fingerprint of a voxel, a number of hidden layers trained to process the MR fingerprint, and an output layer from which at least one MR parameter relating to the MR fingerprint of the voxel is emitted as an output. This achieves the same technical advantages as achieved by the method as claimed in the first aspect.

According to a further aspect of the invention, the object is achieved by a magnetic resonance apparatus for determining MR parameters, having an MR data acquisition scanner that acquires an MR fingerprint of a voxel by execution of a pulse sequence, and a determining processor that determines at least one MR parameter by providing inputting the MR fingerprint as an input into the input layer of a trained neural network, providing the at least one MR parameter relating to the MR fingerprint of the voxel at the output layer of the trained neural network. This achieves the same technical advantages as achieved by the method of the first aspect. A neural network, which is trained, as described in the fourth aspect, is provided in the determining processor as the trained neural network.

In an embodiment of the magnetic resonance apparatus, the magnetic resonance apparatus is designed to determine MR parameters of a large number of adjacent voxels. This has the technical advantage that maps and images of the corresponding MR parameters can be determined.

DESCRIPTION OF THE PREFERRED EMBODIMENTS

Figure 1:
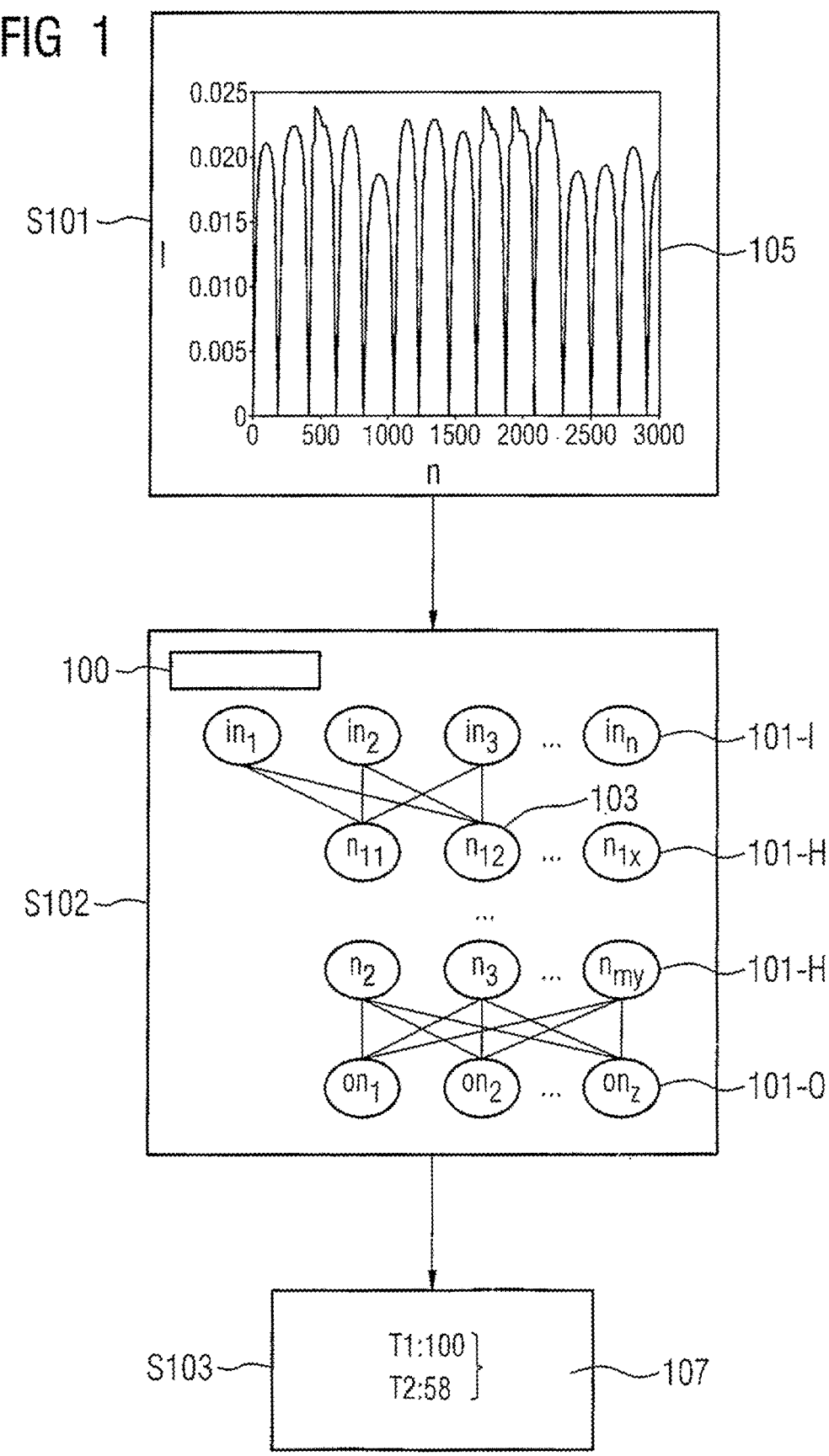
FIG. 1 is a schematic illustration of a neural network and a block diagram of the method for determining MR parameters in accordance with the invention.

FIG. 1 schematically shows a neural network 100. Deep Learning designates a field of machine learning and a category of optimization methods with the aid of artificial neural networks 100, which have numerous intermediate layers 101-H between an input layer 101-I and an output layer 101-O and have an extensive inner structure. The network 100 enables a stable learning success even with numerous intermediate layers 101-H.

The network 100 can be described as an artificial neural network 100 (ANN) having a plurality of hidden layers 101-H. The layers 101-H are used for learning abstract features from the input data. First, features at lower levels and then features at higher levels are learned by the hierarchical representation.

The artificial neural network 100 is based on information processing of the brain. It has a network of calculation units, which are called the nodes 103. The nodes 103 are connected together and can be compared with the neurons and axons in the human brain. Each node 103 receives input data (either as actual input data or as output data from a different node 103), carries out a calculation on the basis of this input data and forwards the result to connected nodes. The connections between the nodes 103 have weights which define how strong the connection is between the respective nodes 103.

A network 100 of this kind can have a number of layers 101, such as a convolution layer, a pooling layer and/or a fully-connected layer. In the case of the convolution layer, not all neurons are connected to the neurons of the previous layer; instead filter kernels are learned. A convolution is performed with the filter kernels and the input data and the result of the convolution is forwarded to the subsequent activation function. In the case of the pooling layer, the resolution is reduced and for example the most relevant signals of an environment (for example 2*2) are retained (max pooling). In the case of the fully-connected layer, all output neurons of the previous layer are connected to all neurons of the fully-connected layer in each case.

After the layers 101, the output value is transferred to an activation function. The input layer 101-I with the input nodes $In_1, \ldots, Inn$ accepts the data, while the output layer 101-O with the output nodes $On_1, \ldots, On_n$ as the final layer provides the final output of the network 100. A plurality of hidden layers 101-H with the nodes $n_{11}, \ldots, n_{mf}$ can be arranged between the input layer 101-I and the output layer 101-O.

Before an artificial neural network 100 can be used for calculating output values from input values, the network has to be trained in order to learn the weights of the connections between the nodes 103 of the layers 101 and the values in the filters of the convolutional Layer. During training of the artificial neural network 100, training data is forwarded by the network 100 and the results are compared with expected ground truth values. A known learning algorithm is back propagation. The error between the results and the expected values is then calculated and the gradient of the error function is used to iteratively change the weights in the artificial neural network 100 and to minimize the errors.

To replace matching of MRF pattern recognition of the acquired time series with those time series which are included in the dictionary, a deep learning method on the basis of the artificial neural network 100 is used instead. The artificial neural network 100 is used to learn the features of an MR time series, in other words an MR fingerprint. The network 100 is then used to determine the quantitative MR parameters, such as, for example, the T1 and/or T2 relaxation times, directly from the input MR fingerprint of a voxel.

In step S101, first the MR fingerprint 105 of a voxel is acquired by execution of a pulse sequence. The fingerprint is formed, for example, by plotting the standardized signal intensity I against the number of data points n. The data points reproduce the course over time of the MR signal when the pulse sequence is used.

In step S102 the MR fingerprint 105 of the voxel is input into the input layer 101-I of the trained neural network 100. For this purpose, the input layer 101-I has a number of n input nodes $In_1, \ldots, In_n$. MR fingerprint 105 is then conveyed through the trained network 100. In step S103 at least one MR parameter, for example T1, T2, of the voxel 107 relating to the MR fingerprint 105 is output at the output layer 101-O of the neural network 100.

Figure 2:
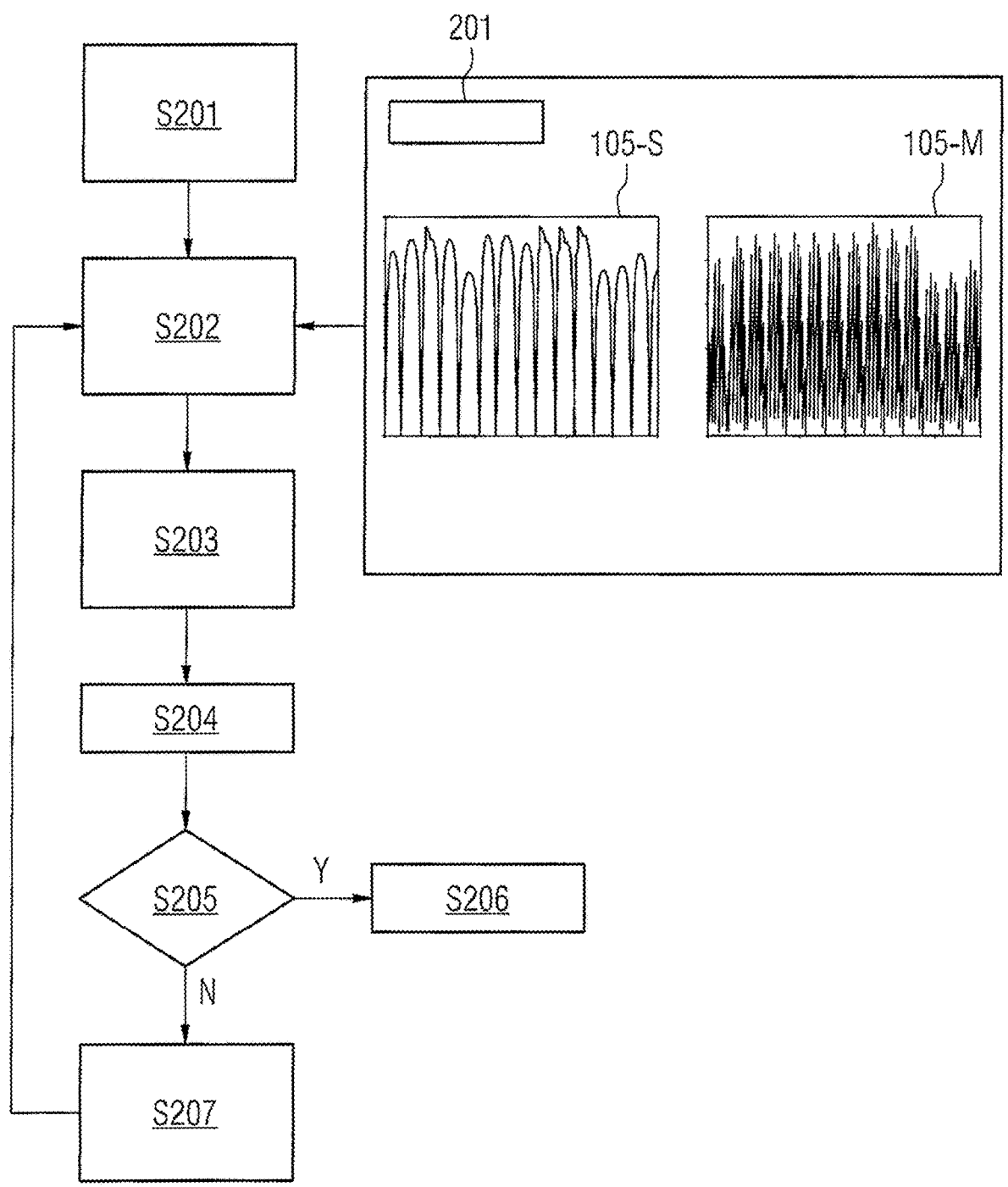
FIG. 2 is a block diagram for training the neural network in accordance with the invention.

FIG. 2 shows a block diagram relating to the training of the neural network 100. An artificial neural network 100 for a regression problem is designed and trained for the architecture of the system. With a regression problem the outputs of the network 100 are continuous numbers, while with a categorization problem the output is the probability of a category or a plurality of probabilities for a plurality of categories respectively.

This network 100 learns the features from the MR time series, in other words MR fingerprints, of different tissue, for example different T1 and T2 combinations, with the aid of a training process and outputs the associated quantitative MR parameters, such as for example T1 or T2 relaxation times. The time series of different T1 and T2 combinations differ in each case. The network 100 has convolutional layers, fully connected layers and non-linear activations. The input into the neural network 100 is a measured time series of the standardized signal intensity of a voxel, in other words the MR fingerprint of the voxel, and the output of the neural network 100 is the quantitative MR parameter.

Training of the artificial neural network 100 is performed with simulated MR time series, in other words MR fingerprints, as the input and the associated MR parameters, with which the simulation has been carried out, as the ground truth values. The data is divided among training, validation and test data sets.

Validation data sets are used to improve the training results by way of a change in hyper parameters of the network 100. The hyper parameters can be, for example, the number of hidden layers in the network, a learning rate, a size and number of the filter kernels, an optimization method and/or a number of neurons per layer. To render the network 100 stable in respect of artifact behavior, such as noise or undersampling artifacts, after completed training with simulated data, training with measured phantom data with known ground truth values, such as, for example, T1 and T2 relaxation times, are used for fine tuning the weights of the network 100. The ground truth values come for example from application of the described matching methods to the measured signals or are existing ground truth values, such as, for example, with a NIST phantom.

In step S201 the weights of the neural network 100 are initialized. For this purpose, for example a normal initialization occurs with random numbers from a Gaussian distribution during training or fine tuning from a stored model.

In step S202 input data 201 are supplied, which can be simulated MR fingerprints 105-S and measured MR fingerprints 105-M. After an initialization of the weights, the input data 201 is channeled as training data sets through the network in the forwards direction. The simulated MR fingerprints 105-S are used during training of the neural network 100. The measured MR fingerprints 105-M are used during fine tuning, In step S203 the results are compared with the ground truth values from the dictionary. The MR parameters, which are assigned to the simulated MR fingerprints 105-S, are used during training. The phantom parameters of the measured MR fingerprints are used during fine tuning.

The errors between the corresponding output of the neural network 100 and the ground truth values are calculated in step S204.

In step S205 a check is made as to whether the predefined number of iterations has been attained or the error lies below a predefined limit. If this is the case, the model of the neural network is stored in step S206.

If this is not the case, the weights of the nodes 103 are updated in the network 100 in step S207 by means of a back propagation and a gradient of the error function.

Figure 3:
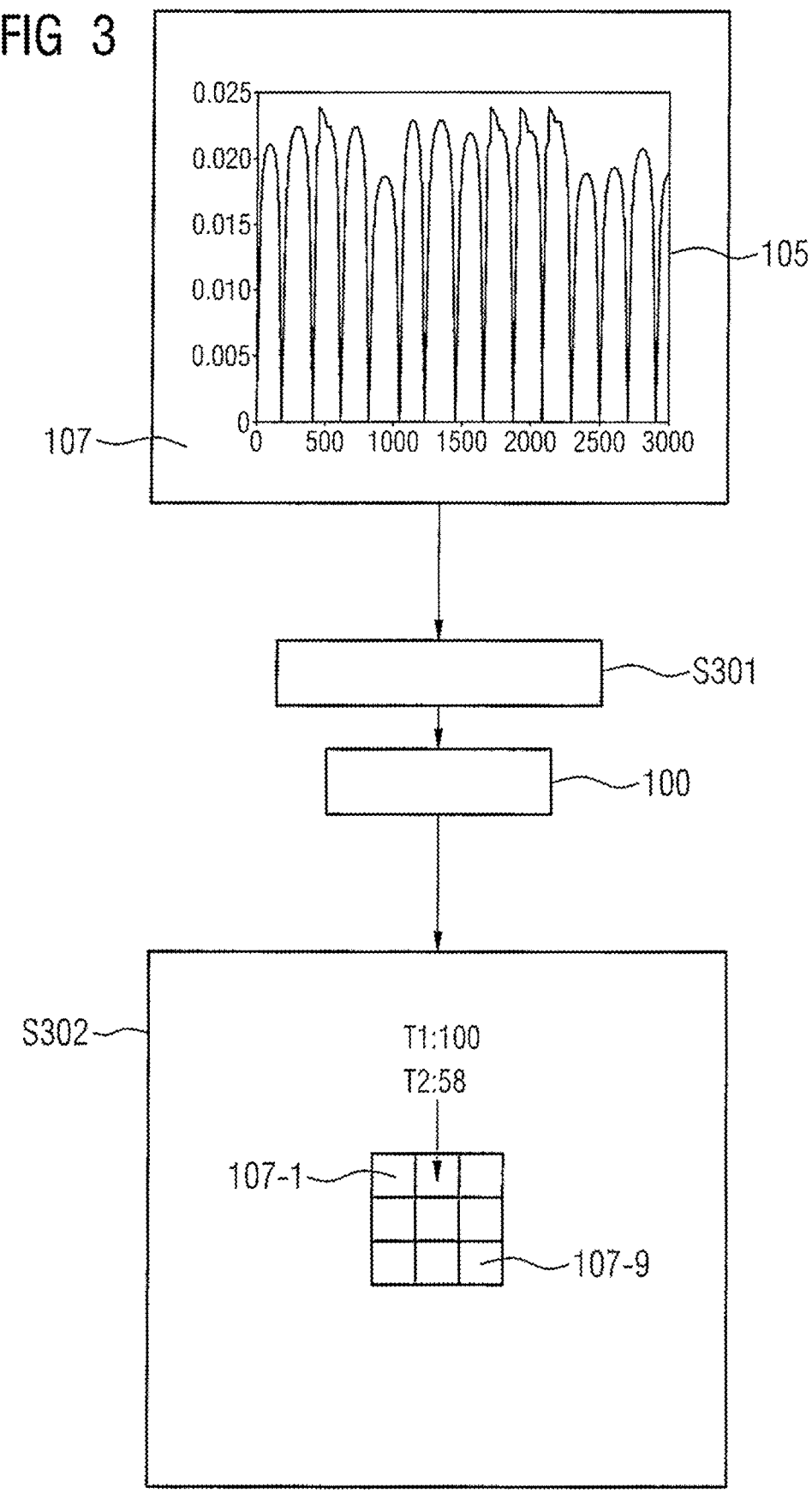
FIG. 3 is a block diagram of a resolution enhancement in accordance with the invention.

FIG. 3 shows a block diagram of a resolution enhancement. In step S301 an MR fingerprint 105 of a single voxel 107 is input into the neural network 100. In step S302 z MR parameters are then output for a number of voxels 107, . . . , 107-9 by the network 100.

The network 100 can be trained to improve a partial volume effect by upsampling the resolution of the MR image or the quantitative maps (super resolution). This can be achieved by training of the network 100, so that it provides an output of, for example, a 3×3 environment of voxels with separate parameter values, which have smaller dimensions accordingly, for an input MR fingerprint 105 of a single voxel 107.

Figure 4:
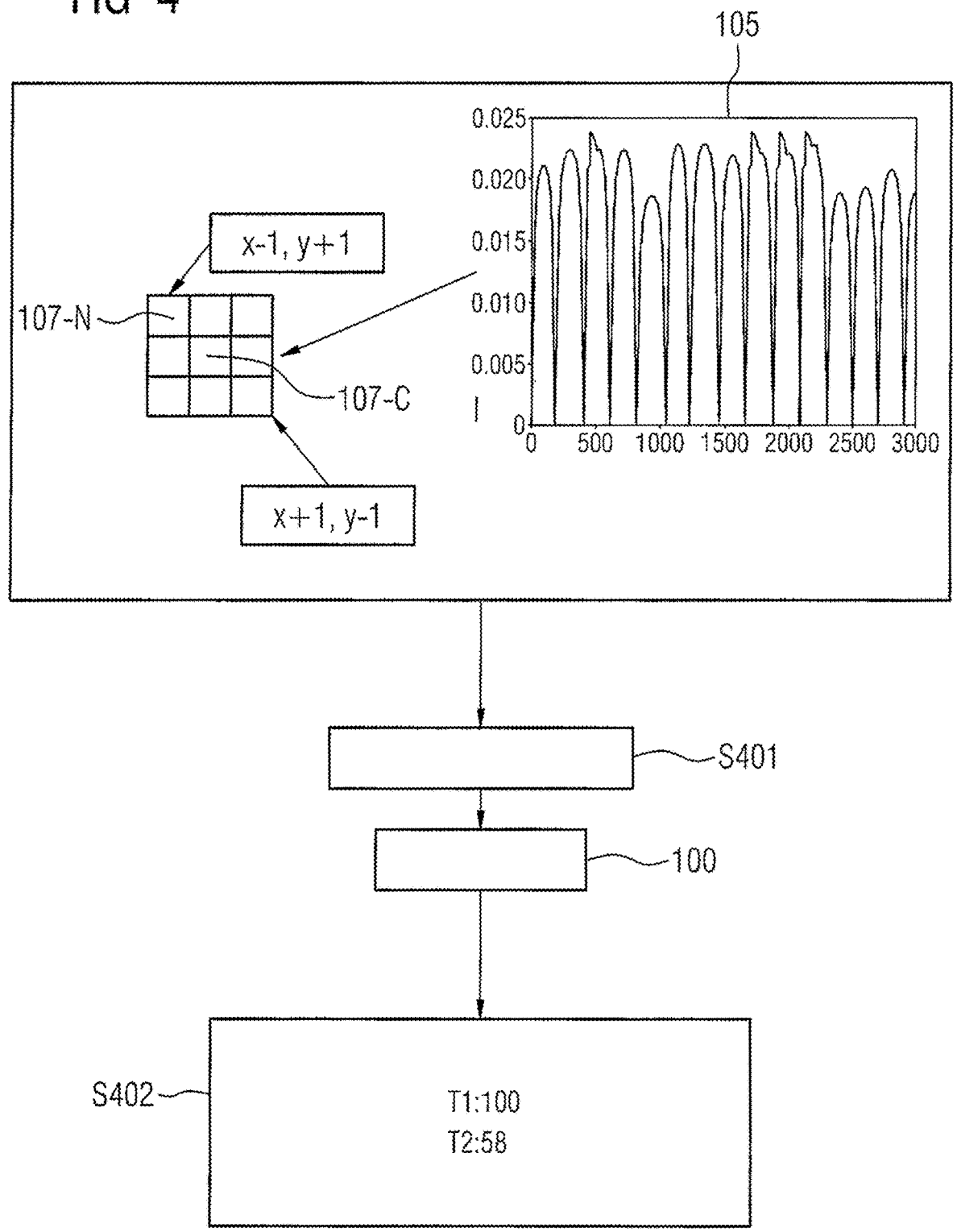
FIG. 4 is a block diagram of consideration of spatial neighbors in accordance with the invention.

FIG. 4 shows a block diagram of consideration of spatial neighbors. The network 100 can be used to likewise consider the spatial context of a voxel 107.

In step S401, for example the MR fingerprints 105 of a central voxel 107-C and the adjacent voxel 107-N are input into the network 100. The MR fingerprint of the central voxel 107-C and its spatial neighbor 107-N are processed to improve prediction of the quantitative MR parameters of the central voxel 107-C. The spatial context can likewise be used to estimate error probabilities in the calculations.

In step S402 the MR parameters for the central voxel 107-C are output by the network 100. By processing an MR fingerprint of a voxel 107, the MR parameters for its spatial neighbors can likewise be predicted.

Figure 5:
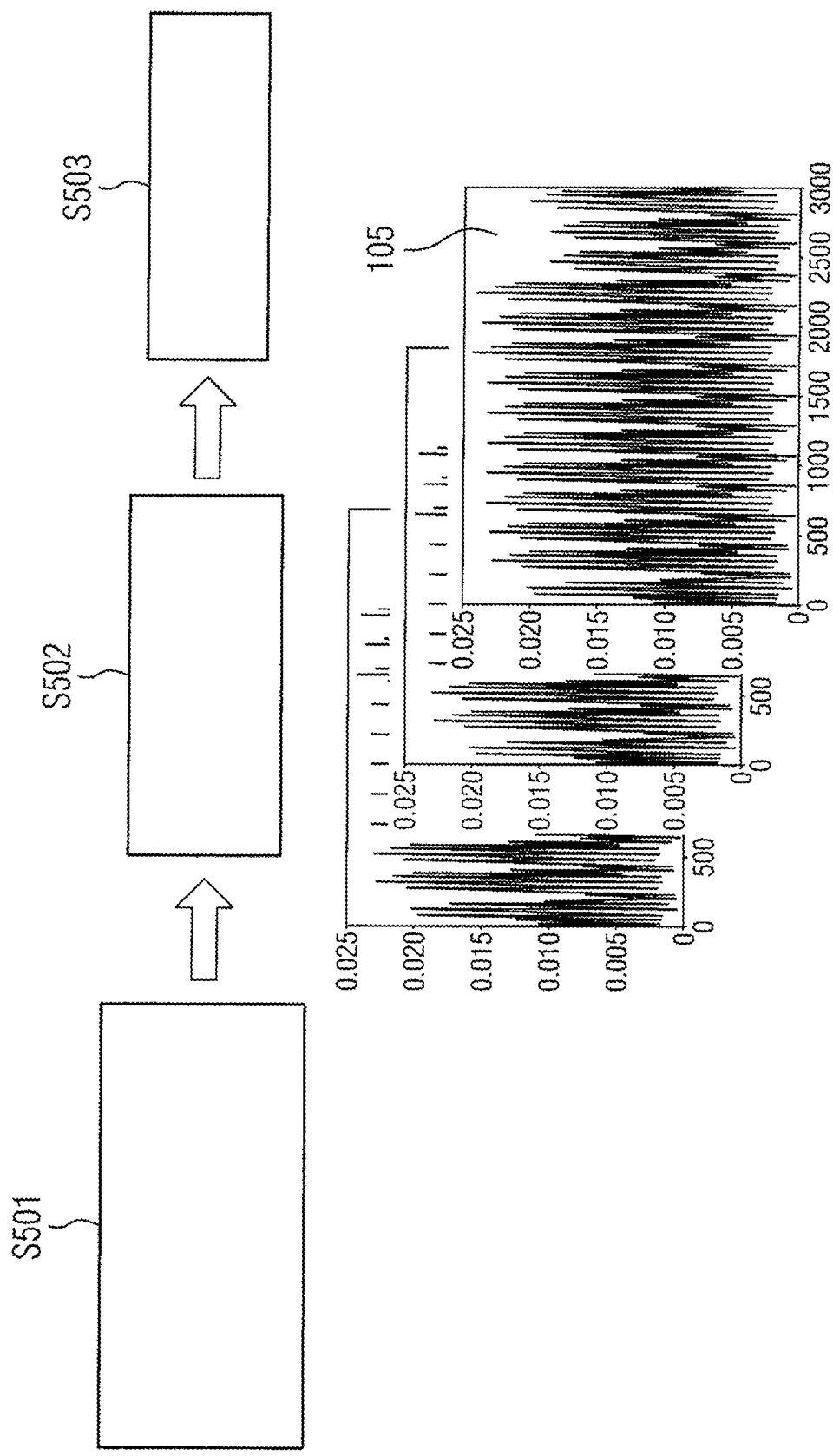
FIG. 5 is a block diagram for generating a recording sequence, measuring time series, and training the neural network in accordance with the invention.

FIG. 5 shows a block diagram for generating a recording sequence, measuring time series and training the neural network. In step S501 a recording rule is generated, such as, for example, a pulse sequence. In step S502 the recording rule is used to measure the MR fingerprint of the voxel 107. In step S503 the network 100 is trained using the measured MR fingerprint.

The design of the network 100 can be linked to the teaching, in other words the neural network of U.S. patent application Ser. No. 14/682,220. The network in patent application U.S. Ser. No. 14/682,220 can then be used to generate an ideal recording sequence, which generates an optimum contrast between two MR fingerprints. These fingerprints can be used for training the network 100 to predict MR parameters.

The combination of an MR fingerprint method with deep learning methods enables direct prediction of quantitative maps, such as, for example T1 and T2 relaxation times, with the use of a trained neural network from the acquired MR fingerprint of the respective voxels. By contrast, the known step of matching an MR fingerprint is based on matching a measured time series with a dictionary of simulated time series.

The method and/or the neural network can be implemented by a digital computer program having program segments for carrying out the method steps when the computer program is run on a computer. For this purpose, the computer comprises a computer-readable storage device for storing the computer program and a processor for processing the computer program. The computer program can in turn be stored on an external data storage device, from which the computer program can be loaded into the internal data storage device of the computer. The external data storage device is for example a CD-ROM, a USB flash storage device or an Internet storage drive.

Figure 6:
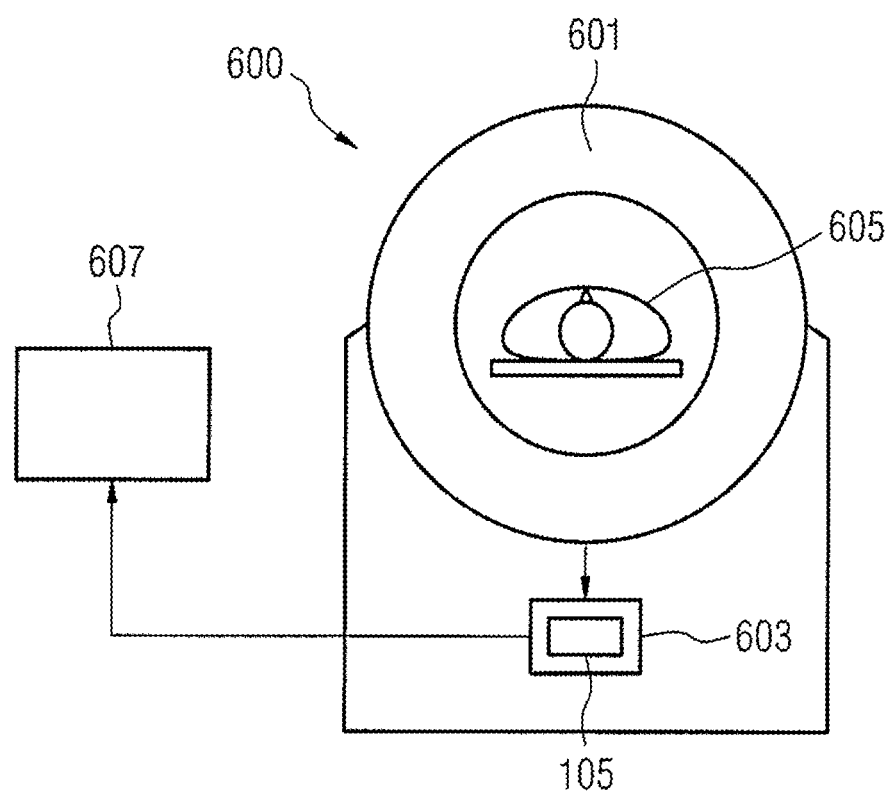
FIG. 6 schematically illustrates a magnetic resonance apparatus for determining MR parameters on the basis of MR fingerprints in accordance with the invention.

FIG. 6 schematically shows a magnetic resonance apparatus 600 for determining MR parameters on the basis of MR fingerprints 105. The magnetic resonance apparatus 600 has a data acquisition scanner 601 that acquires the MR fingerprint 105 of at least one voxel 107 of an examination object by execution of a pulse sequence, for example from a patient 605. The data acquisition scanner 601 has a magnet that generates a basic magnetic field, and a controller that operates an RF antenna and a gradient coil arrangement for applying RF pulses and gradient fields. The data acquisition scanner 601 also has a receiver coil, which detects the MR signals from the excited nuclear spins by currents induced in the coil.

In addition, the magnetic resonance apparatus 600 has a determining processor 603 that determines the MR parameter by providing the measured MR fingerprint 105 as an input into the input layer 101-I of the trained neural network 100 and by providing the at least one MR parameter relating to the MR fingerprint 105 of the voxel 107 at the output layer 101-O of the trained neural network 100. As a result, corresponding MR parameters can be assigned quickly and easily to each voxel, and cross-sections of the patient, for example in a medical examination, can be obtained. The corresponding maps of the determined MR parameters can be displayed on a screen 607.

The determining processor 603 can be formed by a computer module having a digital storage device and a processor, which is capable of executing a computer program for determining the MR parameter. The determining processor 603 can also be implemented by an appropriately designed electronic circuit.

The following advantages can be attained by the magnetic resonance device 600 and the method on the basis of the neural network 100:

1) The speed of quantification is increased. As soon as the artificial neural network 100 is trained, fast calculation of MR parameters is enabled which accelerates assigning of quantitative MR parameters to corresponding voxels 107 compared to the matching methods described above.

2) In addition, the spatial context of a voxel 107 can be considered. The artificial neural network 100 can be trained to not just predict the MR parameters of a single voxel 107, but similarly for the spatial environment of the voxel 107-1, . . . , 107-9. The spatial environment of a single voxel 107-C can be used to obtain a more stable estimation or error estimation.

3) Once the artificial neural network 100 has been trained, a dictionary is no longer required for the step of quantification of the MR parameters. The dictionary is replaced by the neural network 100, which, however, requires less storage space and the storage space requirement of which is not dependent on the number of possible parameter combinations. The artificial neural network 100 can likewise predict any combination of MR parameters, whereas a dictionary only has a limited resolution, and this leads to a high error rate (see for example Wang Z, Zhang Q, Yuan J, Wang X, "MRF Denoising with Compressed Sensing and Adaptive Filtering", Biomedical Imaging (ISBI), 2014 IEEE 11th International Symposium on. IEEE, 2014). Similarly, the storage requirement, simulation time of the dictionary and the time required for matching by means of pattern recognition increase as a function of the resolution of the dictionary. These problems are solved by an artificial neural network 100, which does not use a dictionary or pattern matching methods for calculating the quantitative parameters of a voxel 107.

All features described and illustrated in connection with individual embodiments of the invention can be provided in different combinations in the inventive subject in order to simultaneously achieve the advantageous effects thereof.

All method steps can be implemented by devices which are capable of carrying out the respective method step. All functions, which are performed by concrete features, can be a method step of the method.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining magnetic resonance (MR) parameters, comprising:
   operating an MR data acquisition scanner in order to execute a pulse sequence so as to acquire an MR fingerprint of a voxel of a subject;
   providing the MR fingerprint into an input layer of a trained neural network; and
   operating the neural network to determine at least one of a T1 relaxation time and a T2 relaxation time directly from the MR fingerprint of the voxel, and providing the at least one of the T1 relaxation time and the T2 relaxation time at an output layer of the neural network,
   wherein the determination of at least one of the T1 relaxation time and the T2 relaxation time directly from the MR fingerprint of the voxel is performed without accessing a dictionary of reference signals such that a storage size associated with the trained neural network is a predetermined size.

2. A non-transitory, computer-readable data storage medium encoded with programming instructions, said storage medium being loaded into a computer, comprising a trained neural network, and said programming instructions causing said computer to:
   operate an MR data acquisition scanner in order to execute a pulse sequence so as to acquire an MR fingerprint of a voxel of a subject;
   provide the MR fingerprint into an input layer of a trained neural network; and
   operate the neural network to determine at least one of a T1 relaxation time and a T2 relaxation time directly from MR parameter relating to the MR fingerprint of the voxel, and providing the at least one of the T1 relaxation time and the T2 relaxation time at an output layer of the neural network,
   wherein the determination of at least one of the T1 relaxation time and the T2 relaxation time directly from the MR fingerprint of the voxel is performed without accessing a dictionary of reference signals such that a storage size associated with the trained neural network is a predetermined size.

3. A neural network comprising:
   an input layer configured to receive an MR fingerprint of a voxel;
   a plurality of hidden layers configured to process the MR fingerprint to determine at least one of a T1 relaxation time and a T2 relaxation time directly from the MR fingerprint of the voxel,
   wherein the determination of at least one of the T1 relaxation time and the T2 relaxation time directly from the MR fingerprint of the voxel is performed without accessing a dictionary of reference signals such that a storage size associated with the neural network is a predetermined size; and
   an output layer at which said configured to output the at least one of the T1 relaxation time and the T2 relaxation time.

4. A magnetic resonance (MR) apparatus comprising:
   an MR data acquisition scanner;
   a computer configured to operate said MR data acquisition scanner to execute a pulse sequence so as to acquire an MR fingerprint of a voxel of a subject;
   a neural network comprising an input layer to which MR fingerprint is provided; and
   said neural network comprising an output layer, and said neural network being configured to determine at least one of a T1 relaxation time and a T2 relaxation time directly from the MR fingerprint of the voxel, and to provide the at least one of the T1 relaxation time and the T2 relaxation time at said output layer of the neural network,
   wherein the determination of at least one of the T1 relaxation time and the T2 relaxation time directly from the MR fingerprint of the voxel is performed without accessing a dictionary of reference signals such that a storage size associated with the neural network is a predetermined size.

5. A method as claimed in claim 1 comprising operating the MR data acquisition scanner in order to execute an MRF-FISP pulse sequence, as said pulse sequence.

6. A method as claimed in claim 1 comprising operating said MR data acquisition scanner so as to also acquire MR fingerprints respectively from adjacent voxels that are adjacent to said voxel, and thereby acquiring a plurality of MR fingerprints, and providing said plurality of MR fingerprints into said input layer of said trained neural network, and operating said neural network so as to produce at least one shared parameter, for said plurality of MR fingerprints, at said output layer.

7. A method as claimed in claim 1 comprising providing a single MR fingerprint into said input layer of said trained neural network, and operating said neural network in order to produce a plurality of MR parameters including at least one of the T1 relaxation times and T2 relaxation times for adjacent voxels that are adjacent to said voxel, at said output layer.

8. A method as claimed in claim 1 comprising operating said neural network to evaluate a contrast between two MR fingerprints provided to said input layer of said neural network.

9. A method as claimed in claim 1, wherein the act of operating the MR data acquisition scanner comprises obtaining a time series for an MR signal associated with each respective three-dimensional grid point associated with the voxel.

10. A method as claimed in claim 9, wherein the time series define the MR fingerprint of the voxel of the subject.

11. A method as claimed in claim 1, wherein the act of operating the neural network includes determining, directly from the MR fingerprint of the voxel of the subject, the T1 relaxation time and the T2 relaxation time.

12. A method as claimed in claim 11, wherein a time series define the MR fingerprint of the voxel of the subject, and wherein the T1 relaxation time and the T2 relaxation time are determined using the time series.

13. A method as claimed in claim 10, wherein the act of operating the neural network includes determining at least one of the T1 relaxation time and the T2 relaxation time using a comparison of the time series that define the MR fingerprint of the voxel of the subject with a simulated time series for which MR parameters are known.

14. A method as claimed in claim 1, wherein the act of operating the MR data acquisition scanner further comprises predicting MR parameters in addition to the at least one of the T1 relaxation time and the T2 relaxation time, the MR parameters being associated with a spatial environment occupied by the voxel of the subject.

15. A magnetic resonance apparatus as claimed in claim 4 wherein said computer is configured to operate said MR data acquisition scanner in order to acquire a plurality of MR fingerprints respectively from adjacent voxels that are adjacent to said voxel, and wherein said plurality of MR fingerprints are provided to said input layer of said trained neural network.

* * * * *